(12) United States Patent
Yamada

(10) Patent No.: US 9,204,803 B2
(45) Date of Patent: Dec. 8, 2015

(54) OPTICAL DEVICE, DETECTING APPARATUS, AND ELECTRONIC APPARATUS

(71) Applicant: Seiko Epson Corporation, Tokyo (JP)

(72) Inventor: Kohei Yamada, Suwa (JP)

(73) Assignee: Seiko Epson Corporation (JP)

(*) Notice: Subject to any disclaimer, the term of this patent is extended or adjusted under 35 U.S.C. 154(b) by 72 days.

(21) Appl. No.: 14/227,399

(22) Filed: Mar. 27, 2014

(65) Prior Publication Data

US 2014/0296665 A1    Oct. 2, 2014

(30) Foreign Application Priority Data

Mar. 28, 2013    (JP) .................................. 2013-068252

(51) Int. Cl.
    *G01J 1/42*        (2006.01)
    *A61B 5/00*        (2006.01)
    *G01N 21/65*       (2006.01)

(52) U.S. Cl.
    CPC ............. *A61B 5/0075* (2013.01); *A61B 5/0082* (2013.01); *A61B 5/443* (2013.01); *A61B 5/7282* (2013.01); *A61B 5/743* (2013.01); *G01N 21/65* (2013.01)

(58) Field of Classification Search
    CPC ..... G01N 21/64; G01N 21/65; G01N 21/658; A61B 5/0075
    See application file for complete search history.

(56) References Cited

U.S. PATENT DOCUMENTS

| 8,008,620 | B2 | 8/2011 | Ikeda et al. | |
|---|---|---|---|---|
| 2006/0146323 | A1* | 7/2006 | Bratkovski et al. | 356/301 |
| 2014/0166863 | A1 | 6/2014 | Yamada et al. | |
| 2015/0131092 | A1* | 5/2015 | Sakagami et al. | 356/301 |

FOREIGN PATENT DOCUMENTS

| JP | 2008-249434 A | 10/2008 |
|---|---|---|
| JP | 2009-222401 A | 10/2009 |
| JP | 2010-078482 A | 4/2010 |
| JP | 2013-096939 A | 5/2013 |
| JP | 2014-119263 A | 6/2014 |
| WO | WO-2012-175900 A1 | 12/2012 |

OTHER PUBLICATIONS

Peter Freunscht et al., "Surface-Enhanced Raman Spectroscopy of Trans-Stilbene Absorbed on Platinum- or Self-Assembled Monolayer-Modified Silver Film Over Nanosphere Surfaces", Department of Chemistry, Northwestern University, Evanston, IL 60208, Oct. 31, 1996, pp. 372-378.

(Continued)

*Primary Examiner* — Tony Ko
(74) *Attorney, Agent, or Firm* — Harness, Dickey & Pierce, P.L.C.

(57) ABSTRACT

An optical device includes: a substrate; a metal nanostructure formed on the substrate and containing metal particles; and an organic molecular film formed on the metal nanostructure. A particle size of each metal particle is 1 nm to 500 nm when seen in a plan view. The organic molecular film includes holes penetrating in a thickness direction thereof. The holes are arranged in a two dimensional array along the surfaces of the metal particles. A size α of each hole satisfies $0.5 \text{ nm} \leq \alpha \leq 5$ nm, a period P of the holes satisfies $P \leq 10$ nm, and a thickness t of the organic molecular film satisfies $t \leq 1$ nm.

16 Claims, 13 Drawing Sheets

(56) References Cited

OTHER PUBLICATIONS

Shinobu Uemura et al., "Two-Dimensional Self-Assembled Structures of Melamine and Melem At the Aqueous Solution—Au (111) Interface", Langmuir Article, Graduate School of Science and Technology, Kumamoto University, Kumamoto, Japan, Oct. 1, 2010, pp. 1336-1340.

Yudai Ishikawa et al., "A Two-Dimensional Modecular Network Structure of Acid Prepared by Absorption-Induced Self-Organization", Department of Applied Chemistry and Biochemistry, Faculty of Engineering, Kumamoto University Kumanoto, Japan, Aug. 2, 2002, pp. 2652-2653.

* cited by examiner

OPTICAL DEVICE, DETECTING APPARATUS, AND ELECTRONIC APPARATUS

BACKGROUND

1. Technical Field

The present invention relates to an optical device, a detecting apparatus, an electronic apparatus, and the like.

2. Related Art

Recently, surface enhanced Raman scattering (SERS) spectroscopy using surface plasmon resonance (SPR), particularly, using localized surface plasmon resonance (LSPR) has attracted attention as a high-sensitivity spectroscopy technique for detecting low-concentration target molecules. SERS refers to a phenomenon in which an enhanced electric field is formed between metal particles contained in a nanometer-sized convex and concave structure, and Raman scattering light is enhanced due to the enhanced electric field by, for example, $10^2$ times to $10^{14}$ times. In this technique, single-wavelength excitation light such as laser light is irradiated on target molecules. A scattering wavelength (Raman scattering light), which is slightly shifted from the wavelength of the excitation light by molecular vibration energy of the target molecules, is spectroscopically detected to obtain a fingerprint spectrum. Based on this fingerprint spectrum, an extremely small amount of target molecules can be identified.

The intensity of the enhanced electric field is stronger in the vicinity of metal particles, particularly, in a gap between adjacent metal particles. Therefore, it is necessary that target molecules in a fluid sample be fixed in a gap between metal particles. For example, in JP-A-2009-222401 and P. Freunscht et al., "Surface-enhanced Raman spectroscopy of trans-stilbene adsorbed on platinum or self-assembled monolayer-modified silver film over nanosphere surfaces", Chemical Physics Letters, 281 (1997), 372 to 378, a self-assembled monolayer (SAM) film is formed on a metal surface of a sensor chip.

In FIGS. 10 and 12 of JP-A-2009-222401, the diameter of a metal pattern is 800 nm. In P. Freunscht et al., a silver film is formed on a polystyrene spherical convex portion having a diameter of 542 nm. Moreover, in JP-A-2009-222401 and P. Freunscht et al., a self-assembled monolayer (SAM) film is formed on a metal pattern.

In JP-A-2010-78482, an organic molecular film and a surface modification layer which have a thickness of 0.3 nm to 50 nm are formed over a metal nanosphere. In JP-A-2008-249434, a fine porous polymer film is formed on a metal surface.

In the structures disclosed in JP-A-2009-222401 and P. Freunscht et al., since the density of the metal particles which form a hot site where an enhanced electric field is formed is low, there is a limit in improving the detection capability in a sensor chip.

In addition, the self-assembled monolayer (SAM) disclosed in JP-A-2009-222401 and P. Freunscht et al.; and the organic molecular film and the surface modification layer disclosed in JP-A-2010-78482 make adsorbed target molecules and metal particles distant from each other. The enhanced electric field hot site formed in a gap between the metal particles is significantly attenuated when measured at positions at intervals of 0.1 nm from a metal surface. That is, in order to achieve high-sensitivity SERS detection, it is necessary for the target molecules to be captured in the vicinity of the metal surface.

Meanwhile, in a thiol-based silane coupling agent used in JP-A-2008-249434, regular holes with a size of 10 nm or less which can capture volatile organic compound (VOC) molecules cannot be formed. The assumption in JP-A-2008-249434 is that the hole size is 10 nm to 100 nm (0060). Since this hole size is too large to capture VOC, sufficient detection sensitivity is not obtained. In addition, the porous polymer film disclosed in JP-A-2008-249434 does not include complete through-holes through which a metal surface is exposed. From this point of view, in JP-A-2008-249434, similar to other techniques of the related art, since the enhanced electric field hot site is attenuated at a position distant from the metal surface, there is a limit in improving detection capability.

SUMMARY

An advantage of some aspects of the invention is to provide an optical device, a detecting apparatus, and an electronic apparatus which are capable of enhancing Raman scattering light in a gap between adjacent metal particles to improve detection capability while securing the density of an enhanced electric field hot site.

An aspect of the invention is directed to an optical device including: a substrate; a metal nanostructure that is formed on the substrate and contains plural metal particles; and an organic molecular film that is formed on the metal nanostructure, in which a particle size of the plural metal particles is 1 nm to 500 nm when seen in a plan view in a thickness direction of the organic molecular film, the organic molecular film includes plural holes penetrating in the thickness direction, the plural holes are arranged in a two dimensional array along surfaces of the metal particles, a size α of the plural holes satisfies 0.5 nm≤α≤5 nm, a period P of the plural holes satisfies P≤10 nm, and a thickness t of the organic molecular film satisfies t≤1 nm.

According to this aspect, one or plural target molecules having the respective sizes of 1 nm or less (most of which are about 0.4 nm to 0.6 nm) enter into the holes having the size α and are adsorbed on the metal particles and the organic molecular film to be in contact with multiple points. At this time, the organic molecular film includes the holes which are arranged facing a gap between two adjacent metal particles, and the target particles which are adsorbed on the metal particles in the holes are positioned in a hot site of an enhanced electric field. In addition, since the period P of the holes is small at 10 nm or less, the density of capturing spots of the target molecules present in the hot site is secured. Since the thickness t of the organic molecular film is small at 1 nm or less, the number of atoms contributing to an electric field direction is less than or equal to 10 atoms. Therefore, the amount of Raman signal noise made by the organic molecular film itself is small. Accordingly, only Raman scattering light of the target molecules in the gap between the adjacent metal particles is enhanced, and the detection capability can be improved.

In the optical device of the aspect of the invention, a distance between two adjacent metal particles among the plural metal particles may be 0.1 nm to 20 nm. As a result, a strong hot site can be secured in a gap between two adjacent metal particles. When the distance between the adjacent metal particles is greater than the above-described range, the interaction between the adjacent metal particles is decreased, an enhanced electric field to be formed is weakened, and thus a function as a hot site deteriorates.

In the optical device of the aspect of the invention, the thickness t of the organic molecular film may satisfy t≤0.5 nm. As a result, the number of atoms contributing to an electric field direction is less than or equal to 5 atoms, and noise to a SERS signal can be minimized.

In the optical device of the aspect of the invention, the organic molecular film may have a honeycomb structure. As a result, the holes are regularly arranged at the predetermined period P along a two-dimensional direction (in a two dimensional array).

In the optical device of the aspect of the invention, the organic molecular film may include plural building block molecules and adjacent pairs of the building block molecules bind to each other, each of the building block molecules may have, as a basic molecule for forming a high-order compound, a three-fold rotation axis in a molecular center when seen in a plan view in the thickness direction of the organic molecular film, and three terminals of each of building block molecules which are present at positions rotationally symmetrical to the molecular center may be functional groups. By six of such building block molecules binding to each other, a honeycomb structure can be formed.

In the optical device of the aspect of the invention, the plural building block molecules may include one type of molecule among trimesic acid molecules, melem molecules, or melamine molecules or may include both the melem molecules and the melamine molecules. By six of such building block molecules binding to each other, a honeycomb structure can be formed. In addition, since these building block molecules form a self-assembled film on the metal particles, film peeling or the like can be prevented.

(7) Another aspect of the invention is directed to a detecting apparatus including: a light source; the optical device according to any one of the foregoing aspects on which light emitted from the light source is incident; and a light detector that detects light emitted from the optical device. In this detecting apparatus, the detection sensitivity is improved by using the above-described optical device.

Still another aspect of the invention is directed to an electronic apparatus including: the detecting apparatus according to the above aspect; a calculating unit that calculates health medical (diagnostic) information based on detection information obtained from the detecting apparatus; a storing unit that stores the health medical information; and a display unit that displays the health medical information. This electronic apparatus is useful for medical diagnosis, inspection of food and drink, and the like.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Hereinafter, a preferred embodiment of the invention will be described in detail. It should be noted that the embodiment described below does not unreasonably limit the content of the invention described in the appended claims, and all the configurations described in the embodiment are not essential to solutions provided by the invention.

1. Optical Device 1.1 Summary of Optical Device

Figure 1:
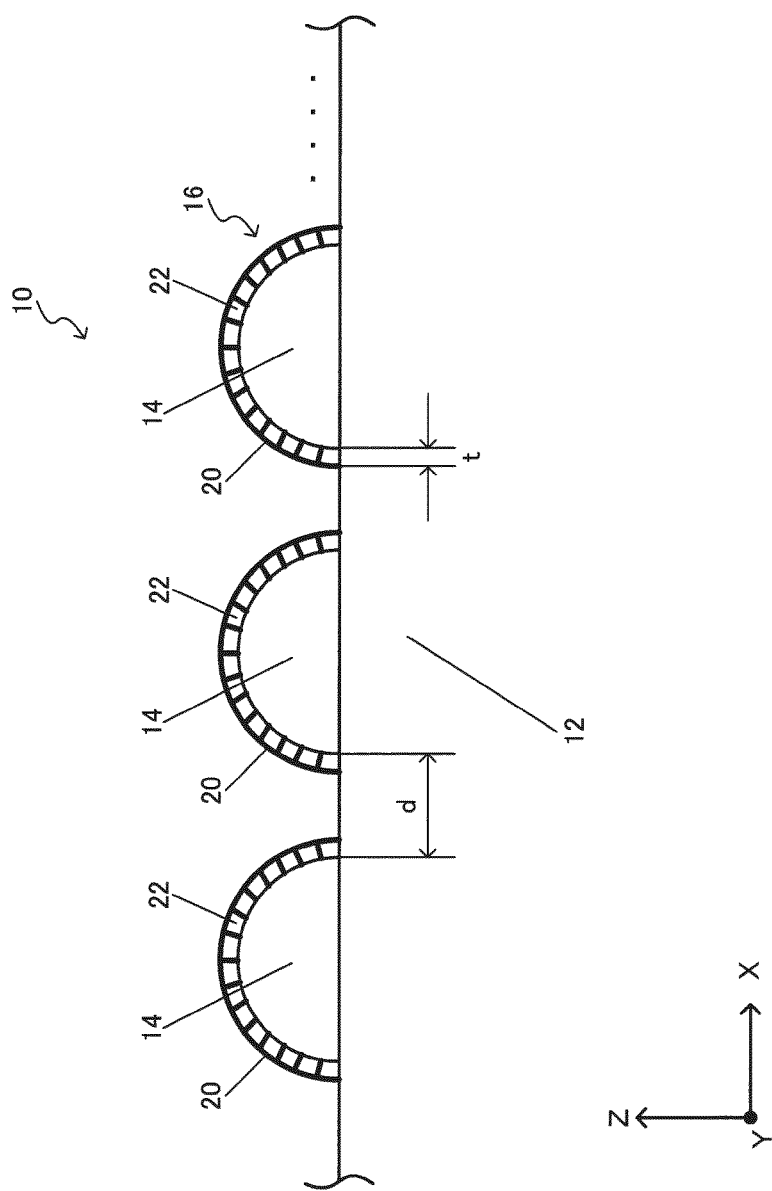
FIG. 1 is an image schematically illustrating an optical device according to an embodiment of the invention.
Figure 2:
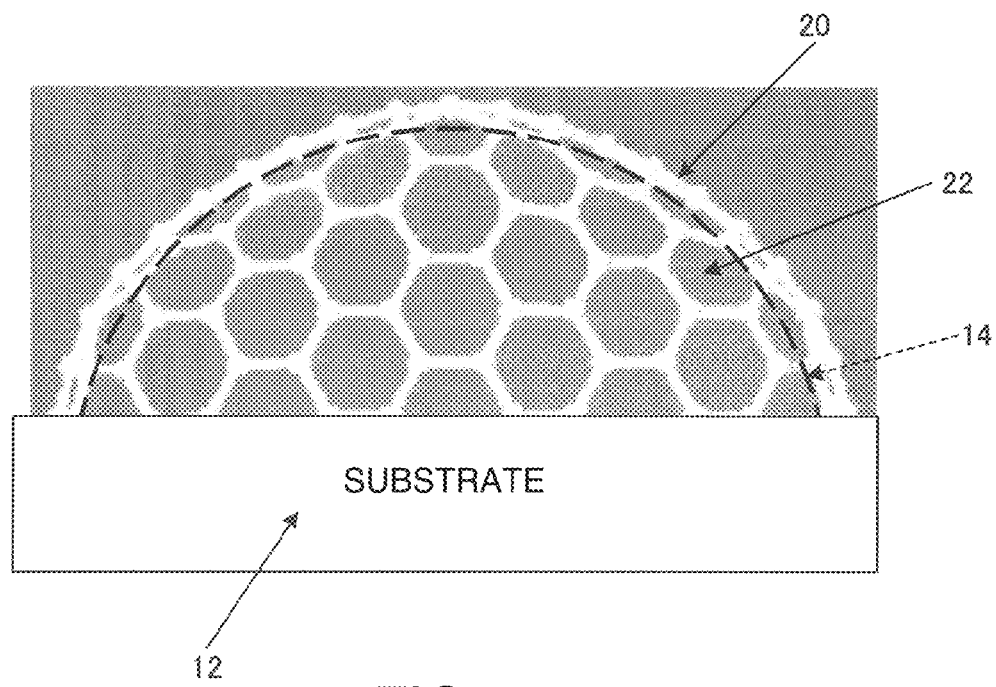
FIG. 2 is an enlarged image illustrating a metal particle of FIG. 1 when seen from the front.
Figure 3:
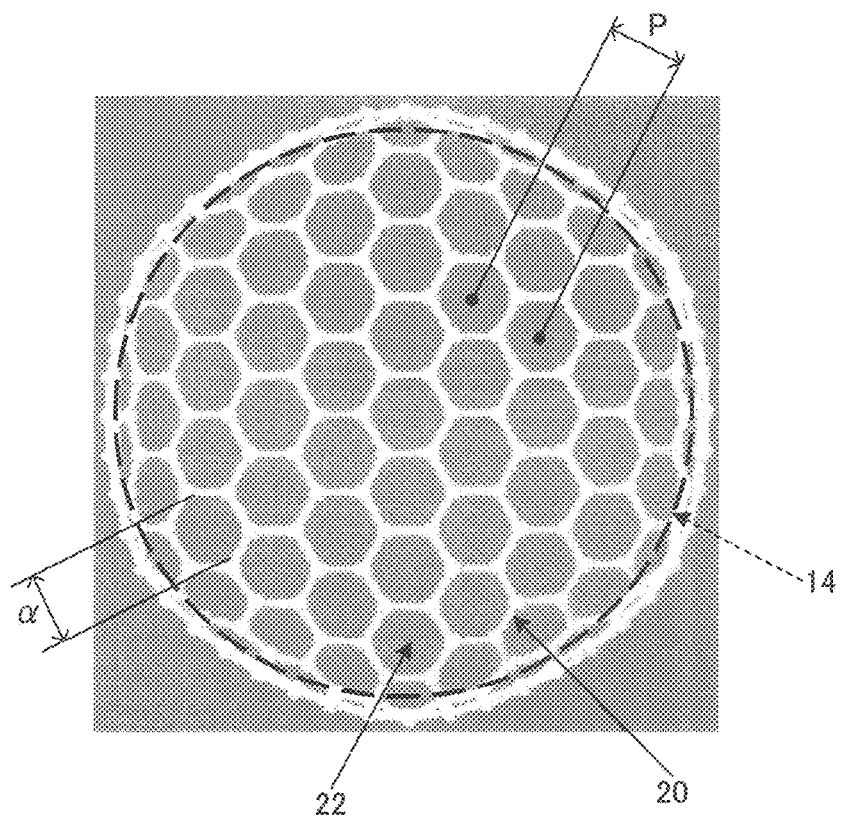
FIG. 3 is an enlarged image illustrating a metal particle of FIG. 1 when seen in a plan view.

FIG. 1 is an image schematically illustrating an optical device 10 according to an embodiment of the invention. In particular, FIGS. 1 to 3 are images drawn for visually illustrating the embodiment, in which the dimensions of the respective portions and the ratios between the dimensions are largely different from the actual ones. The outermost surface of a substrate 12 of FIG. 1 is, for example, a dielectric. A metal nanostructure 16 including plural metal particles 14 is provided on the surface of the substrate 12. In the metal nanostructure 16, the metal particles 14 are arranged on an X-Y plane of FIG. 1, for example along X and Y axes. Each metal particle 14 is a metal nanoparticle having a particle size of 1 nm to 500 nm when seen in a plan view in a Z direction.

FIG. 2 is an enlarged front view illustrating one of the metal particles 14 of FIG. 1, and FIG. 3 is a plan view thereof. As illustrated in FIG. 1, an organic molecular film 20 is formed on the metal nanostructure 16. As illustrated in FIGS. 1 to 3, the organic molecular film 20 includes plural holes 22 penetrating in a thickness direction of the organic molecular film.

The holes 22 are arranged to expose a two-dimensional surface (the outermost surfaces of the metal particles 14). Thus, the holes extend in a direction which intersects with the thickness direction of the metal particles 14. In FIGS. 2 and 3, the relationships between the sizes of the regions of the organic molecular film 20 other than the holes 22, the size α of the holes 22, and the size of the metal particles 14 are illustrated such that the ratios thereof are different from the actual ones for drawing convenience.

The size α and the period P of the holes satisfy 0.5 nm≤α≤5 nm and P≤10 nm, respectively. In addition, the thickness t of the organic molecular film 20 of FIG. 1 satisfies t≤1 nm. In addition, the distance d between two adjacent metal particles 14 of FIG. 1 can be 0.1 nm to 20 nm. The organic molecular film 20 according to the embodiment has a honeycomb structure as illustrated in FIGS. 2 and 3. The operations based on the dimensions of the metal particles 14 and the organic molecular film 20 will be described below.

1.2 Metal Nanostructure

Figure 4A:
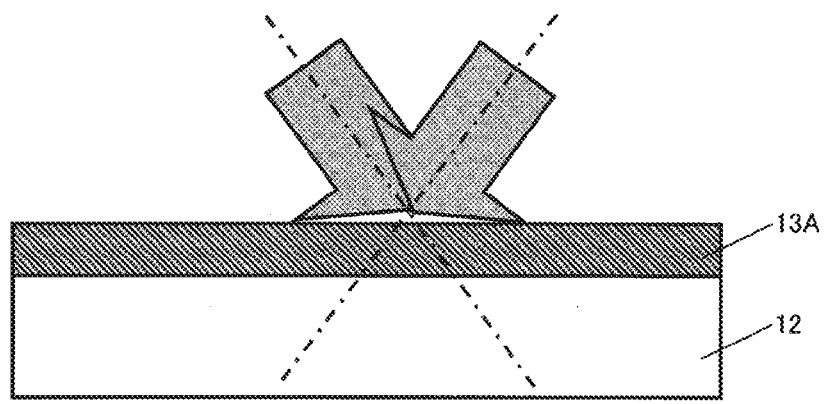
FIGS. 4A to 4E are diagrams illustrating a manufacturing process of a metal nanostructure which forms a SERS sensor chip.
Figure 4B:
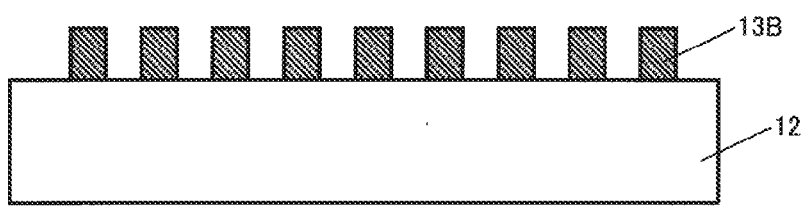
Figure 4C:
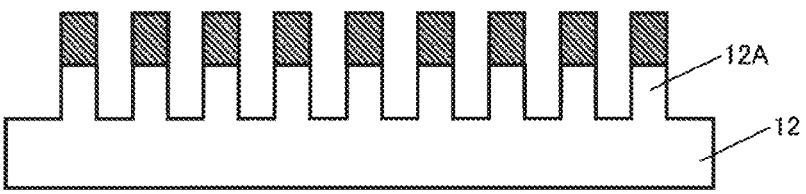
Figure 4D:
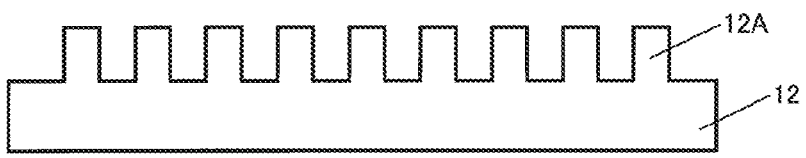
Figure 4E:
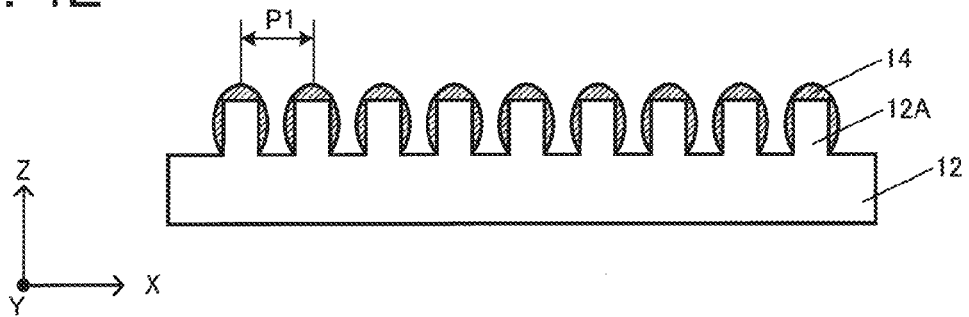

FIGS. 4A to 4E illustrate a manufacturing process of the metal nanostructure 16 which forms a SERS sensor chip. As the substrate 12, any metal, semiconductor, and dielectric can be used. However, in the embodiment, a glass substrate is used. The LSPR metal nanostructure 16 for developing SERS is arranged on the substrate 12. As illustrated in FIG. 4A, a resist 13A is coated on the substrate 12, and deep ultraviolet (DUV) interference exposure is performed twice. As a result, as illustrated in FIG. 4B, a dot-shaped (perforated) mask 13B is formed along a two-dimensional plane (X-Y plane). Using this dot-shaped mask 13B, the substrate 12 is anisotropically etched. As a result, as illustrated in FIG. 4C, dots 12A (posts or bumps) are formed on the surface of the substrate 12. After removing the dot-shaped mask 13B, for example, Ag is deposited on the dots 12A to have a thickness of about 30 nm. As a result, as illustrated in FIG. 4E, the SPR metal nanostructure 16 including the plural metal particles 14 is formed. The period P1 of the metal particles 14 is, for example, 140 nm.

Figure 5:
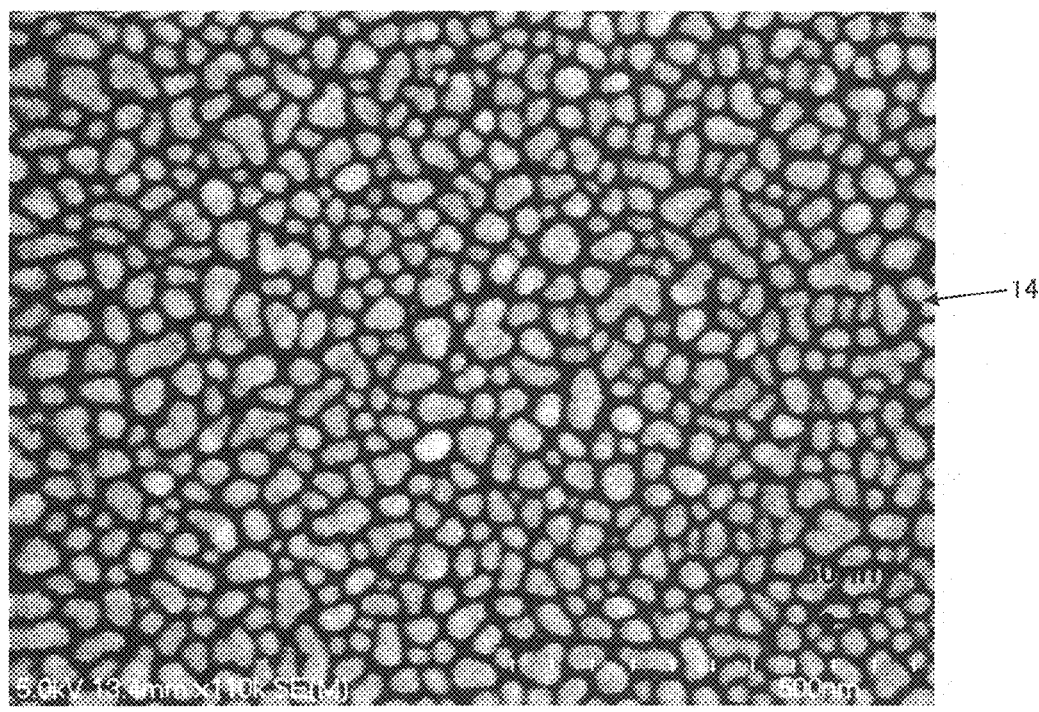
FIG. 5 is a diagram illustrating a metal nanostructure formed by vacuum deposition.

FIGS. 4A to 4E illustrate a manufacturing method using photolithography, but any method can be used as long as it can develop LSPR. For example, simply by depositing Ag on the glass substrate 12 to have a thickness of about 10 nm at 0.1 A/sec to 1.0 A/sec, a SERS sensor substrate for developing LSPR can be manufactured. FIG. 5 is an SEM image of the manufactured substrate. Ag nanoparticles (metal particles) 14 having a particle size of about 30 nm to 100 nm are formed.

Figure 6:
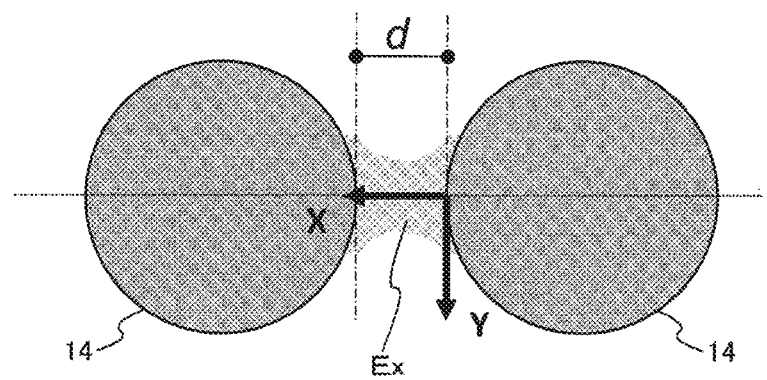
FIG. 6 is a diagram illustrating a hot site formed in a gap between two adjacent metal particles.

1.3 Electric Field Attenuation Based on Distance from Metal Surface 1.3.1 First Comparative Example FIG. 6 is a plan view of a First Comparative Example illustrating a metal nanostructure in which, for example, the metal particles 14 having a diameter of 50 nm are arranged in the X and Y directions at intervals of 5 nm. In FIG. 6, only two metal particles 14 which are adjacent to each other in the X direction are illustrated.

FIG. 6 illustrates a distribution of an electric field $E_X$ in the X direction between the two metal particles 14 when light polarized in the X direction is incident from the Z axis, which is perpendicular to the X-Y plane, toward the metal nanostructure 16 on the substrate 12. When the metal particles 14 having a particle size of 1 nm to 500 nm less than the wavelength of the incident light are irradiated with the incident light, an electric field of the incident light acts on free electrons present on the surfaces of the metal particles 14 to cause resonance. As a result, the electric dipole caused by the free electrons is excited in the metal particles 14, an enhanced electric field stronger than the electric field of the incident light is formed. The above-described phenomenon is localized surface plasmon resonance (LSPR). In surface enhanced Raman scattering (SERS), it is reported that the detection sensitivity is proportional to the fourth power of the electric field. Accordingly, the intensity of an enhanced electric field $E_X$ in the X direction contributing to the sensitivity is expressed by $|E_X|^4$, and the electric field intensity of an enhanced electric field $E_Y$ in the Y direction contributing to the sensitivity is expressed by $|E_Y|^4$.

Figure 7:
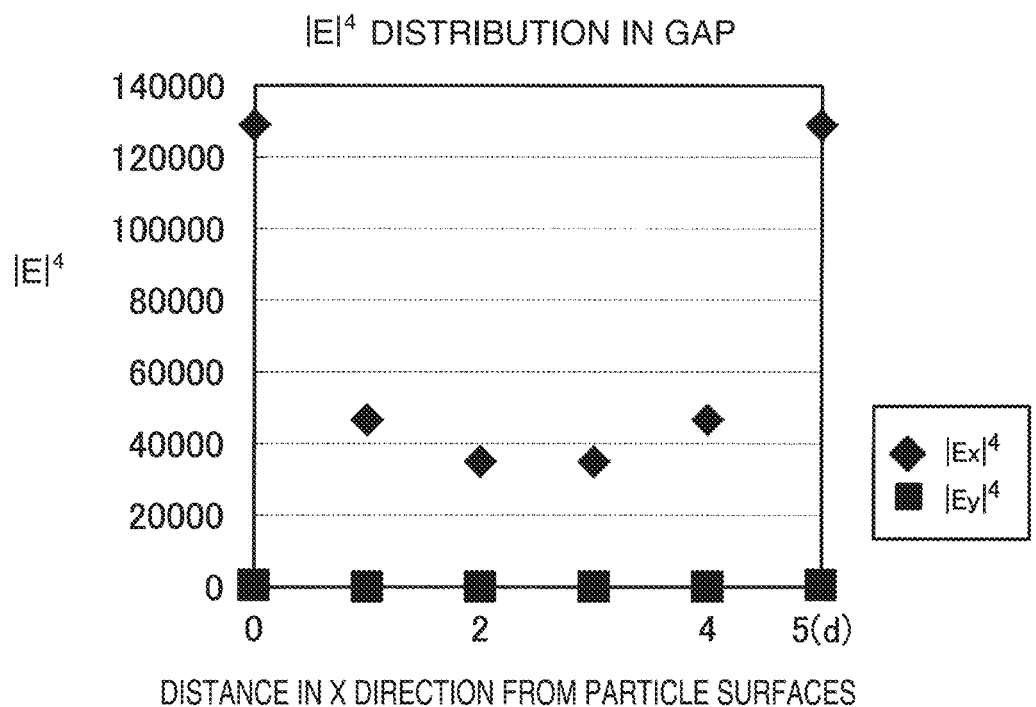
FIG. 7 is a diagram illustrating the positional dependency of detection sensitivity in the hot site of FIG. 6.

FIG. 7 illustrates the results of the electric field intensity ($|E_X|^4$) in the X direction and the electric field intensity ($|E_1|^4$) in the Y direction which are obtained by the finite-difference time-domain (FDTD) method in a gap between the two metal particles 14 of FIG. 6 in the X direction. As clearly seen from FIG. 7, the electric field intensity $|E_X|^4$ in the X direction formed in the gap between the metal particles 14 is maximized on a metal surface and is significantly attenuated with distance from the metal surface in units of 0.1 nm. In the hot site between the two metal particles 14 adjacent to each other in the X direction, the electric field intensity $|E_X|^4$ in the X direction is predominant, and the electric field intensity $|E_Y|^4$ in the Y direction does not substantially contribute thereto. Conversely, when incident light polarized in the Y direction is used, in a hot site between two adjacent metal particles 14 adjacent to each other in the Y direction, the electric field intensity $|E_Y|^4$ in the Y direction is predominant, and the electric field intensity $|E_X|^4$ in the X direction does not substantially contribute thereto.

In surface enhanced Raman scattering (SERS), when target molecules enter into an enhanced electric field between two adjacent metal particles 14, Raman scattering light caused by the target molecules is enhanced in the enhanced electric field, and the signal intensity of the Raman scattering light is increased. As a result, even if the amount of the target molecules 1 is small, the detection sensitivity can be increased. As can be seen from FIG. 7, when the target molecules are adsorbed on the surfaces of the metal particles 14, the signal sensitivity is maximized.

However, when the target molecules are molecules of, for example, a volatile organic compound (VOC) such as acetone or toluene, these target molecules are not chemically adsorbed but physically adsorbed on the surfaces of the metal particles 14 and thus are easily desorbed from the surfaces of the metal particles 14. Accordingly, the detection sensitivity is not increased based on FIG. 7.

1.3.2 Second Comparative Example

Therefore, in JP-A-2009-222401, JP-A-2010-78482, JP-A-2008-249434, and P. Freunscht et al., "Surface-enhanced Raman spectroscopy of trans-stilbene adsorbed on platinum or self-assembled monolayer-modified silver film over nanosphere surfaces", Chemical Physics Letters, 281 (1997), 372 to 378, a polymer film such as SAM is formed on the surfaces of metal particles to make target particles physically adsorbed thereon. However, even in this case, the target particles are not adsorbed on the surfaces of the metal particles but on the surface of the polymer film. Accordingly, there is a limit in improving signal sensitivity based on FIG. 7.

Figure 8:
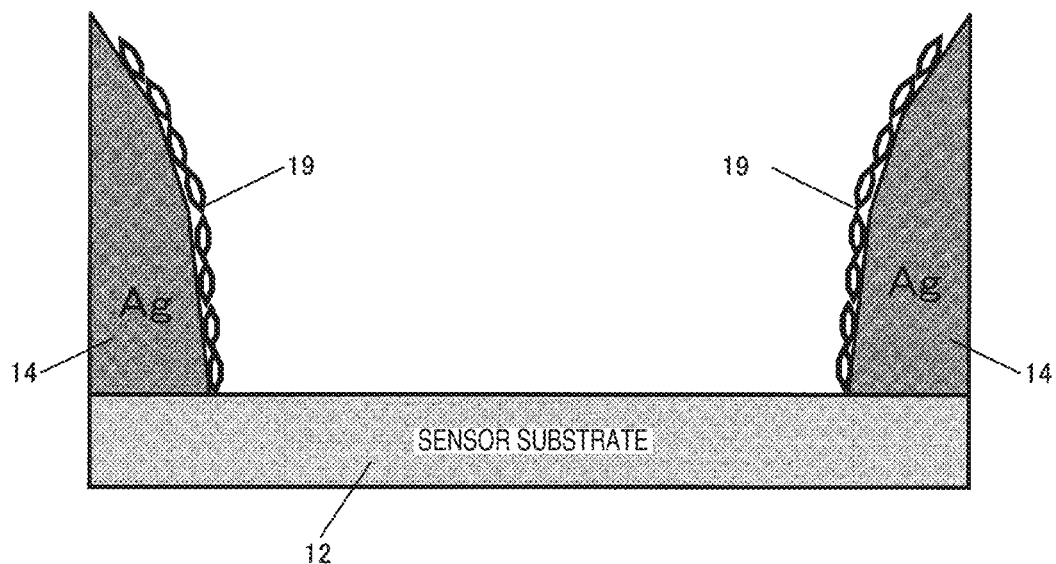
FIG. 8 is a diagram illustrating a sensor chip structure of the related art in which metal particles are covered with a fine porous polymer film.

In JP-A-2008-249434, a fine porous polymer film is provided on a metal surface. However, as illustrated in FIG. 8, the fine porous polymer film 19 does not include complete through-holes through which the surfaces of the metal particles 14 are exposed. Accordingly, since target molecules are distant from the surfaces of the metal particles 14 by the thickness of the fine porous polymer film 19, it is difficult to obtain the desired detection sensitivity.

Figure 9:
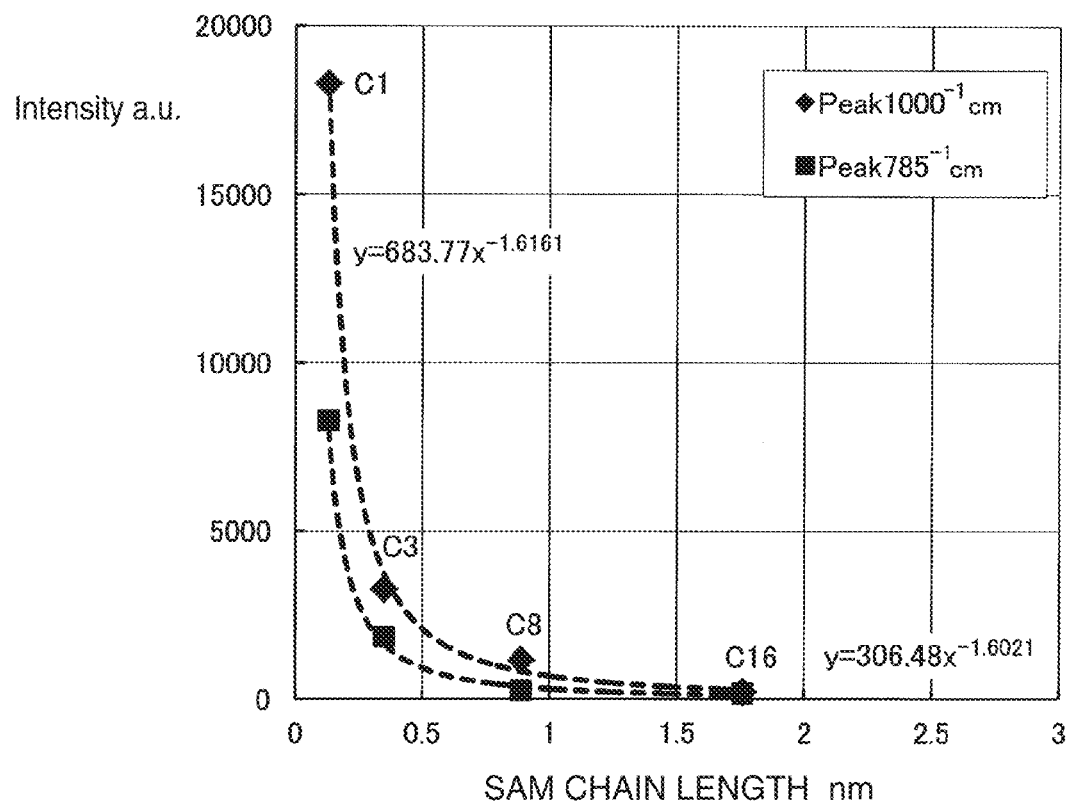
FIG. 9 is a characteristic diagram illustrating the SERS intensity of toluene when a sensor chip, in which metal particles are covered with organic molecules having various chain lengths, is exposed to toluene molecular vapor.

In FIG. 9, the SERS intensity of toluene is plotted when a sensor chip, in which Ag nanospheres (metal particles) are covered with alkanethiol molecules having various chain lengths, is exposed to toluene molecular vapor. The shorter the chain length, the stronger the SERS intensity. As the number of carbon atoms is increased, the SERS intensity is exponentially attenuated. Similarly to FIG. 6, FIG. 9 illustrates a state where the hot site is attenuated when measured at positions at intervals of 0.1 nm from the metal spherical surface. That is, in order to achieve high-sensitivity SERS detection, it is desirable that target molecules be captured on the surfaces of the metal particles 14.

1.4 Operation of Device According to Embodiment 1.4.1 Size of Holes

When target molecules are molecules of a volatile organic compound (VOC) such as acetone or toluene, the size of the target molecules is about 0.4 nm to 0.6 nm, and most of VOC molecules are less than or equal to 1 nm. As a space size for capturing these molecules, the size corresponding to 1.5 molecules to 10 molecules is preferable. This is because the target molecules are adsorbed on the metal particles 14 or the organic molecular film 20 at not one point but multiple points of each molecule.

In the embodiment, the organic molecular film 20 covering the metal particles 14 includes the holes 22 penetrating in the thickness direction thereof, and one or plural VOC molecules enters into the holes 22. At this time, the target molecules are adsorbed not only on the surfaces of the metal particles 14 but on the organic molecular film 20.

Typically, as the number of adsorption points is increased, the intermolecular interaction becomes stronger. As a result, the target molecules are more strongly adsorbed. Accordingly, target molecules such as VOC molecules, which are immediately desorbed in the one-point adsorption due to the weak physical adsorption force, can be fixed on the surfaces of the metal particles 14 by the multi-point adsorption. The target molecules of the embodiment are not limited to VOC molecules. This is because the adsorption force of any molecule can be increased by the multi-point adsorption.

In the embodiment, since the organic molecular film 20 covering the metal particles 14 includes the holes 22 penetrating in the thickness direction thereof, the target molecules which enter into the holes 22 reach the surfaces of the metal particles 14. Further, the target molecules are adsorbed on the surfaces of the metal particles 14 and the organic molecular film 20 at multiple points and are fixed on the surfaces of the metal particles 14. As a result, as illustrated in FIG. 6, a SERS signal can be detected even on the surfaces of the metal particles 14 with the highest sensitivity. Accordingly, in the embodiment, the sensitivity is improved by one or two digits as compared to a SERS detection technique of the related art using, for example, an alkanethiol SAM.

1.4.2 Period of Holes

When the size α of the holes 22 is small, the number of target particles captured in the hot site area is small unless a large number of holes 22 are provided in the hot site. Therefore, it is difficult to obtain sufficient detection sensitivity. In order to solve this problem, in the embodiment, a large number of holes 22 are regularly arranged in a two dimensional array on a surface (the surfaces of the metal particles 14), which intersects with the thickness direction of the organic molecular film 20. Since the hot site is present in a local region with several tens of nanometers along a gap surface between metal nanoparticles, the period P (FIG. 2) of the holes 22 is preferably less than or equal to 10 nm. In addition, as long as the period P is greater than the size α of the holes 22, the smaller the period P, the better.

1.4.3. Thickness of Organic Molecular Film

Figure 10:
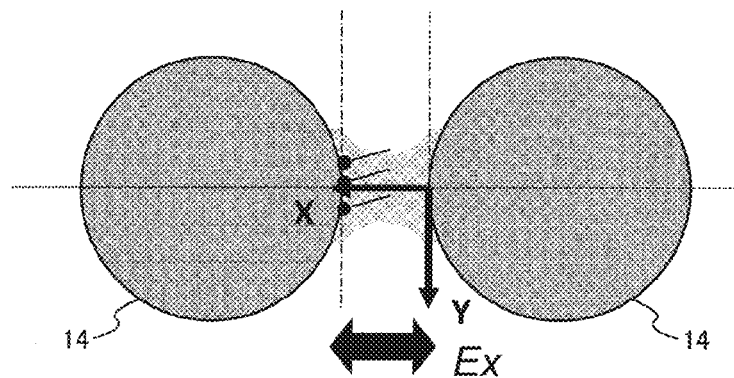
FIG. 10 is a diagram illustrating a state where molecules having a molecular orientation, which matches with a direction of an electric field Ex, are adsorbed on metal particles.
Figure 11:
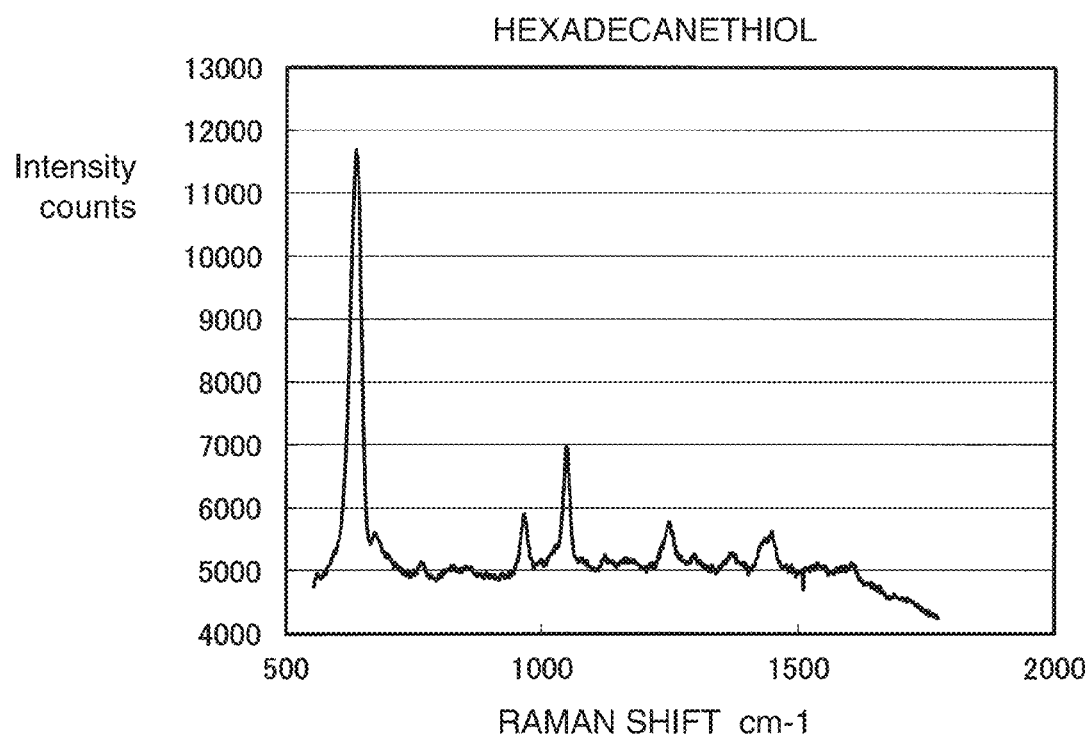
FIG. 11 is a diagram illustrating a SERS signal of the molecules of FIG. 10.

The electric field of the hot site of FIG. 6 is an $E_X$ component. Accordingly, SERS is excited in the electric field of the $E_X$ component. This phenomenon implies that a SERS signal is generated or not generated depending on the orientation of adsorbed molecules. For example, as illustrated in FIG. 10, hexadecanethiol molecules ($CH_3$—$(CH_2)_{15}$—SH) are vertically adsorbed on Ag particles or Au particles, which are the metal particles 14, through S atom-metal bonds. That is, the direction of molecular dipole moment matches with the $E_X$ direction. Therefore, hexadecanethiol molecules which are adsorbed on metal particles 14 facing the hot site generate a SERS signal of FIG. 11. Accordingly, by detecting a Raman signal having a specific wavelength, hexadecanethiol molecules can be identified.

Figure 12:
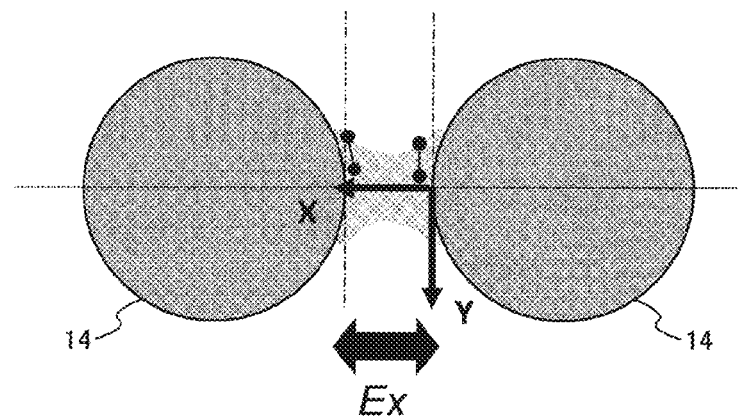
FIG. 12 is a diagram illustrating a state where molecules having a molecular orientation, in a direction which intersects with a direction of an electric field Ex, are adsorbed on metal particles.
Figure 13:
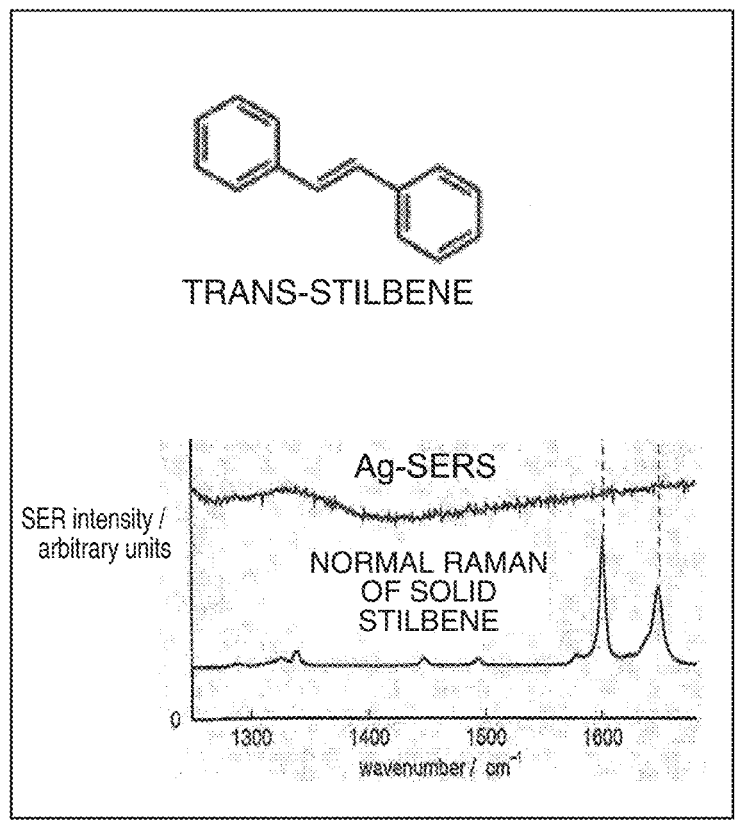
FIG. 13 is a diagram illustrating a SERS signal of the molecules of FIG. 12.

On the other hand, as illustrated in FIG. 12, it is considered that trans-stilbene molecules ($C_6H_5$—CH=CH—$C_6H_5$) are adsorbed on a benzene ring plane and a metal surface in a manner that a π electron of a benzene ring interacts with a metal. As a result, the stilbene molecules are adsorbed on the metal particles 14 to be perpendicular to (intersect with) the $E_X$ component. As a result, as illustrated FIG. 13, a Raman spectrum specific to stilbene molecules which is illustrated in the lower section is not detected, and the peak wavelength is not observed in an Ag-SERS signal which is illustrated in the upper section.

The descriptions which are made using FIGS. 10 to 13 can be applied not only to the target molecules but to the organic molecular film without exception. Raman scattering light of the organic molecular film 20 induced by the $E_X$ component functions as a noise signal which is clearly different from the signal of the target molecules. Therefore, it is preferable that the molecular film does not have a vibration direction which is the same as the EX direction, that is, the thickness t (FIG. 1) of the organic molecular film 20 is less than or equal to 1 nm. When the thickness t of the organic molecular film 20 is less than or equal to 1 nm, the number of atoms contributing to the $E_X$ direction is less than or equal to 10 atoms, and the contribution of noise signal components is decreased. The thinner the thickness t, the better. For example, when the thickness t is less than or equal to 0.5 nm, the number of atoms is less than 5 atoms, and noise signal components are decreased. Accordingly, a sensor substrate suitable for a SERS sensor can be provided.

1.4.4 Distance Between Metal Particles

The distance d between adjacent metal particles 14 can be in a range of 0.1 nm≤d≤20 nm although d=5 nm in FIG. 6. As a result, a strong hot site can be secured in a gap between two adjacent metal particles 14. When the distance between the adjacent metal particles is greater than the above-described range, the interaction between the adjacent metal particles is decreased, an enhanced electric field to be formed is weakened, and thus a function as a hot site deteriorates.

1.5 Organic Molecular Film

Representative examples of the organic molecular film 20, which is formed of organic molecules two-dimensionally arranged on the metal surface, include a monolayer film formed of alkanethiol molecules or silane-based molecules in which the respective molecules are adsorbed in the same form. In addition, the organic molecular film 20 may be a type in which each molecule functions as a building block such that all the molecules form one two-dimensional periodic arrangement structure. In the embodiment, the latter organic molecule film can be preferably used.

The organic molecular film 20 can have a honeycomb structure. As a result, the holes 22 are regularly arranged at the predetermined period P along the two-dimensional direction.

Examples of the building block molecule include a molecule including a three-fold rotation axis in the molecular center, in which three terminals present at positions symmetrical to the molecular center are functional groups with which hydrogen bonds are likely to be formed. By six building block molecules binding to each other through hydrogen bonds, the organic molecular film 20 having a honeycomb structure can be constructed. By providing the holes 22 at the center of the honeycomb structure, the holes 22 can be regularly arranged at the predetermined period P.

Figure 14:
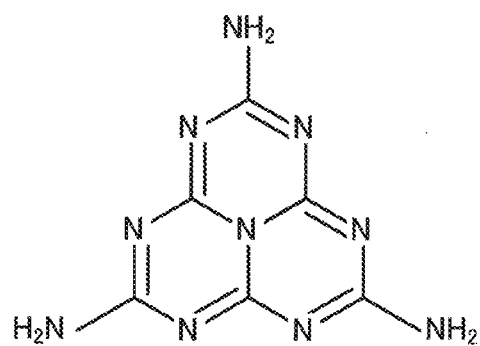
FIG. 14 is a diagram illustrating a molecular structure of a melem molecule which is a building block molecule of a honeycomb structure.
Figure 15:
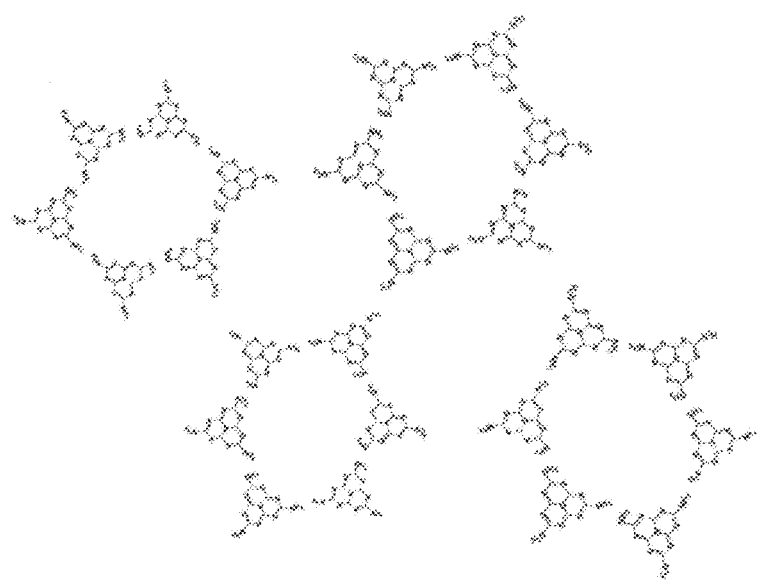
FIG. 15 is a diagram illustrating a honeycomb structure formed by melem molecules.

FIG. 14 illustrates a molecular structure when a melem molecule is selected as the building block molecule (reference article; Langmuir 2011, 27, 1336 to 1340). This molecule has a three-fold rotation axis in the molecular center, in which three terminals present at positions symmetrical to the molecular center are $NH_2$ groups (functional groups) with which hydrogen bonds are likely to be formed. By six melem molecules binding to each other, as illustrated in FIG. 15, a regular honeycomb structure can be formed due to high molecular symmetry. The thickness t of the polymer film 20 formed as above is 0.2 nm in which the contribution of the $NH_2$ groups is large, which satisfies t≤0.5 nm.

Figure 16:
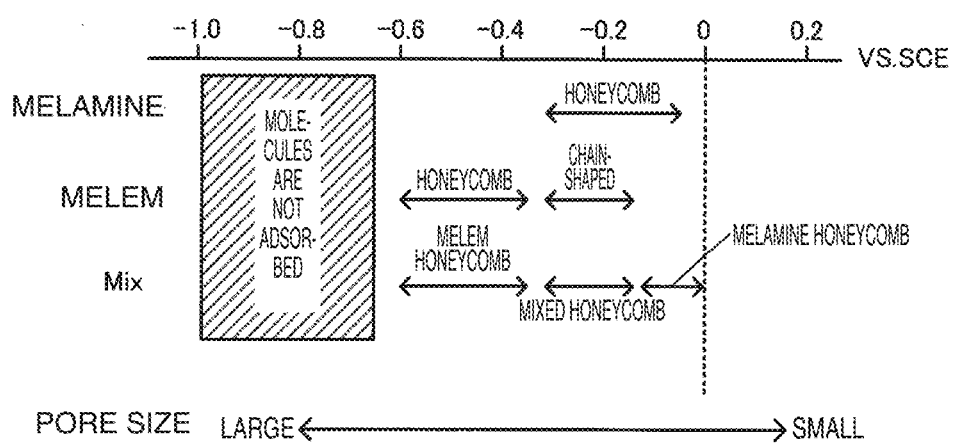
FIG. 16 is a diagram illustrating various structures which are formed by building block molecules while changing a potential difference between a SERS substrate and a reference electrode.

The bonding structure of the plural melem molecules can be observed using a scanning tunnel microscope (STM) and low energy electron diffraction (LEED). In addition, as illustrated in FIG. 16, the bonding structure formed by the plural molecules can be electrochemically controlled. During the formation of the organic molecular film 20, sodium perchlorate is used as an electrolyte, and pH thereof is adjusted to 8 with an aqueous NaOH solution. Melem molecules are dissolved in the aqueous electrolyte solution adjusted above, and a SERS substrate is arranged in an electrode. A potential difference between the SERS substrate and the reference electrode is changed in a range from −1.0 V to 0 V. A honeycomb structure is formed in a range from −0.6 V to −0.4 V, and the honeycomb structure is collapsed into a closed-pack structure in a range of lower than −0.4 V. In addition, the size α of the holes 22 of the honeycomb structure is about 2.2 nm. The period P is about 2.5 nm.

Figure 17:
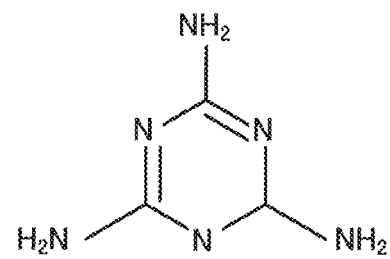
FIG. 17 is a diagram illustrating a molecular structure of a melamine molecule which is a building block molecule of a honeycomb structure.

As a method of further increasing the size α of the holes 22, a solution in which melamine molecules are mixed with melem molecules can be used as building block molecules. FIG. 17 illustrates a melamine molecule. For example, when a mixed solution (melamine:melem=1:3) is used, as illustrated in FIG. 16, only melem molecules form a honeycomb structure in a range from −0.6 V to −0.4 V, and both the melem molecules and the melamine molecules form a mixed honeycomb structure at −0.2 V. At −0.1 V, only melamine molecules form a honeycomb structure. The size α of the holes 22 of the mixed honeycomb structure is about 4 nm, and the size α of the holes 22 of the melamine honeycomb structure is about 1.5 nm which is less than that of the holes of the melem honeycomb structure. The period P of the holes 22 of the melamine honeycomb structure is about 1.8 nm. In this way, building block molecules can be selected in consideration of the size α and the period P of the holes 22.

Figure 18:
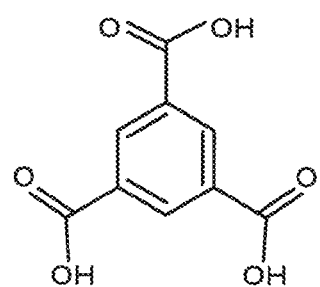
FIG. 18 is a diagram illustrating a molecular structure of a trimesic acid molecule which is a building block molecule of a honeycomb structure.
Figure 19:
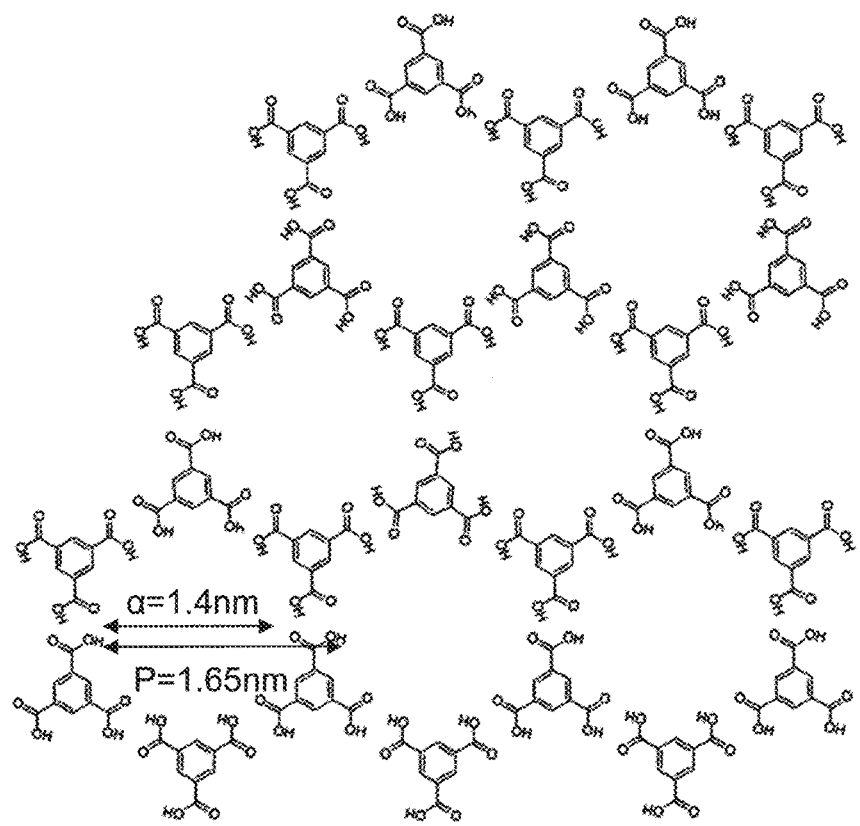
FIG. 19 is a diagram illustrating a honeycomb structure formed by trimesic acid molecules.

The building block molecules are not limited to melem molecules and/or melamine molecules as long as they satisfy two requirements: high symmetry; and functional groups for causing an intermolecular interaction such as hydrogen bonding at corner portions. For example, trimesic acid ($C_6H_3(COOH)_3$) can also be used (Chem. Comm., 22, 2652 (2002)). As illustrated in FIG. 18, a trimesic acid molecule is a highly symmetric molecule having a benzene ring in the center, in which COOH groups, which are likely to cause an intermolecular interaction, bind to coordination sites "1,3,5". The thickness t in a direction perpendicular to the benzene ring plane is less than or equal to 0.3 nm in which the contribution of the COOH groups is large. As in the case of melem molecule, the molecular structure can be formed by controlling a potential. At −0.25 V, as illustrated in FIG. 19, six trimesic acid molecules form a honeycomb structure. At this time, the size α and the period P of the holes 22 are about 1.4 nm and about 1.7 nm, respectively.

2. Detecting Apparatus and Electronic Apparatus

Figure 20A:
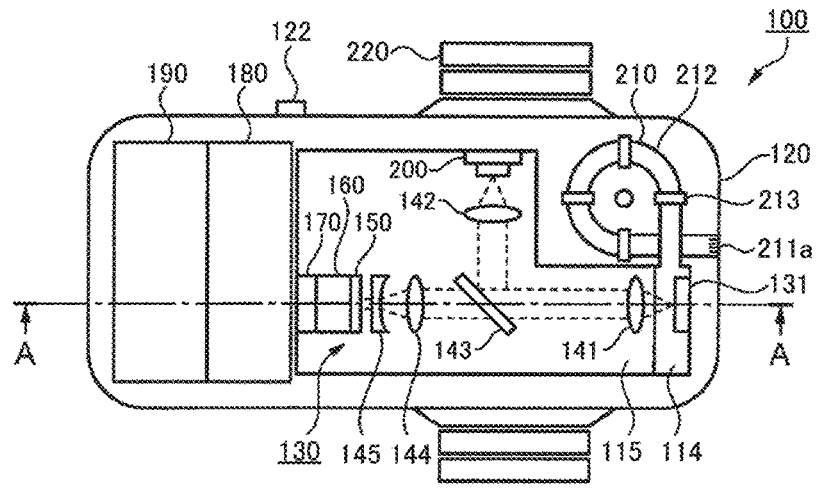
FIGS. 20A to 20C are diagrams illustrating a material detecting apparatus.
Figure 20B:
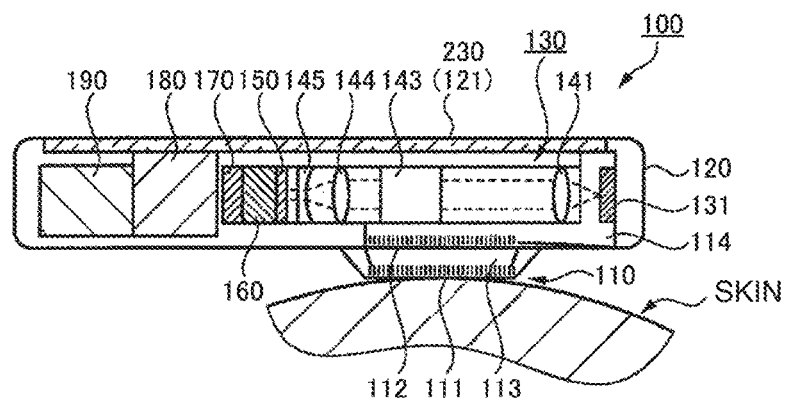
Figure 20C:
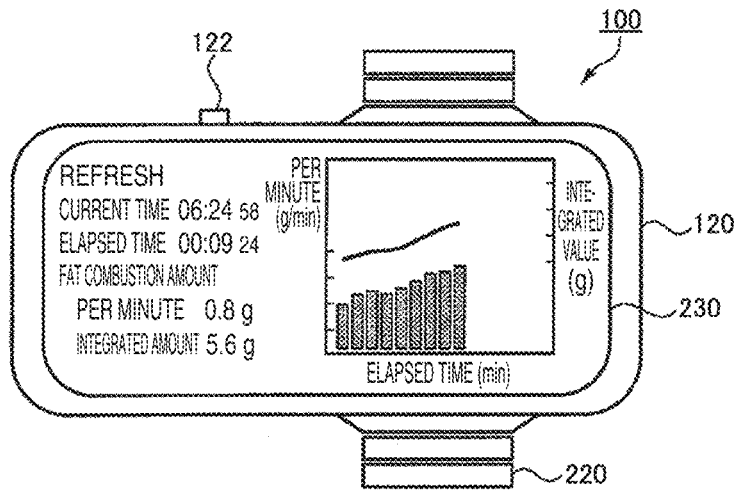

As an example of a detecting apparatus or electronic apparatus 100, a material detecting apparatus for detecting the acetone concentration in biological gas to detect the combustion amount of body fat correlating to the detected acetone concentration will be described. In the material detecting apparatus 100, as illustrated in FIGS. 20A to 20C, a detection sample collecting unit 110, a detecting unit 130, and a display unit 230 are stored in a space formed by a case 120 and a windshield glass 121. The detection sample collecting unit 110 is arranged on a side (back surface side of the case 120) contacting human skin, the detecting unit 130 is arranged inside the case 120, and the display unit 230 is arranged at a position (front surface side of the case 120) that is visible by a test subject.

The detection sample collecting unit 110 includes a first permeable film 111 that comes into close contact with human skin; and a second permeable film 112 that is arranged with a space 113 interposed between the first permeable film 111 and the second permeable film 112. The first permeable film 111 that comes into close contact with human skin has water repellency so as to prevent moisture such as sweat from directly entering into the detecting unit 130; and is formed of a film capable of allowing biological gas (also referred to as "skin gas") produced from the skin to permeate therethrough. The first permeable film 111 is provided for preventing moisture or the like contained in the biological gas from being adsorbed on a sensor unit 131 (described below) when the biological gas is introduced into the detecting unit 130.

The second permeable film 112 has the same function as that of the first permeable film 111 and is provided for forming a double structure with the first permeable film 111 to further strengthen the above-described function of the first permeable film 111. Accordingly, the double structure of the permeable films is not necessarily provided and can be selected depending on, for example, the swear rate of the human body at a position of wearing the material detecting apparatus 100.

The first permeable film 111 and the second permeable film 112 are attached on the human body side of the case 120 such that the first permeable film 111 is brought into close contact with the skin by an apparatus belt 220. The material detecting apparatus 100 illustrated in FIGS. 20A to 20C has an exemplary configuration of a case of being worn around the wrist.

The configuration of the detecting unit 130 will be described. As illustrated in FIGS. 20A and 20B, the detecting unit 130 is divided into a sensor chamber 114 and a detecting chamber 115. The sensor chamber 114 is a space that accommodates biological gas emitted from the arm. The sensor unit 131 is arranged inside the sensor chamber 114. The sensor unit 131 includes the optical device 10 that enhances Raman scattering light.

The detecting chamber 115 includes a light source 200 that excites detection target molecules; a first lens group that collects light irradiated from the light source 200 into the sensor unit 131; and a second lens group that collects enhanced Raman scattering light scattered from the sensor chip 132.

The first lens group includes a lens 142 that converts light emitted from the light source 200 into parallel light; a half mirror 143 that reflects the parallel light toward the sensor unit 131; and a lens 141 that collects the light reflected from the half mirror 143 into the sensor unit 131. The second lens group includes a lens 144 that collects Raman light, which is enhanced in the sensor unit 131, through a lens 141 and a half mirror 143; and a lens 145 that converts the collected Raman light into parallel light.

Further, the detecting chamber 115 includes an optical filter 150 that removes Rayleigh scattering light from the collected scattering light; a spectroscope 160 that disperses the enhanced Raman scattering light into a spectrum; a light receiving element (light detector) 170 that converts the dispersed spectrum into an electrical signal; a signal processing control circuit 180 that converts the dispersed spectrum into an electrical signal as fingerprint spectrum information specific to a material detected from the biological gas; and a power supply 190. The fingerprint spectrum is stored in advance in the signal processing control circuit 180.

As the power supply 190, a primary battery, a secondary battery, or the like can be used. In the case of a primary battery, a CPU 181 compares the obtained voltage information of the primary battery with information stored in a ROM and then, when the voltage is lower than a predetermined value, controls the display unit 230 to display a battery change indication. In the case of a secondary battery, the CPU 181 compares the obtained voltage information of the secondary battery with information stored in a ROM and then, when the voltage is lower than a predetermined value, controls the display unit 230 to display a battery change indication. Based on this indication, the test subject connects a battery charger to a connection portion (not illustrated) to charge the material detecting apparatus 100 until a predetermined voltage is reached. As a result, the material detecting apparatus 100 can be repetitively used.

In addition, the material detecting apparatus 100 according to the embodiment includes a collected sample discharge unit 210 that discharges the biological gas collected inside the sensor chamber 114 to the outside. The collected sample discharge unit 210 includes an elastic discharge tube 212 one end of which is connected to the sensor chamber 114 and the other end of which is connected to a discharge port 211a; and plural rotary rollers 213. The collected sample discharge unit 210 is a so-called tube pump in which the gas in the sensor chamber 114 can be discharged to the outside by the rotary rollers 213 pressing the discharge tube 212 from the sensor chamber 114 to the discharge port 211a.

The tube pump may have a manual rotation structure or a motor-driven structure. As the collected sample discharge unit, any gas discharge units other than the tube pump can be appropriately selected and used. In addition, it is preferable that the discharge port to which the biological gas is discharged from the sensor chamber 114 be provided at multiple positions in order to rapidly discharge the biological gas.

Next, the indications of the display unit 230 will be described with reference to FIG. 20C. The display unit 230 is formed of an electrooptical display element such as a liquid crystal display. Examples of main indications include, as illustrated in FIG. 20C, the current time, the elapsed time from the start of the measurement, the fat combustion amount such as the combustion amount per minute and the integrated value thereof, and the graph indicating changes of the fat combustion amount. In addition, after the measurement of the fat combustion amount, it is desirable that the gas in the sensor chamber 114 be removed (that is, the sensor chip 132 be refreshed), and the indication for notifying the necessity to an operator is also displayed. For example, when "refresh" is displayed, a collected sample discharging operation is performed.

Figure 21:
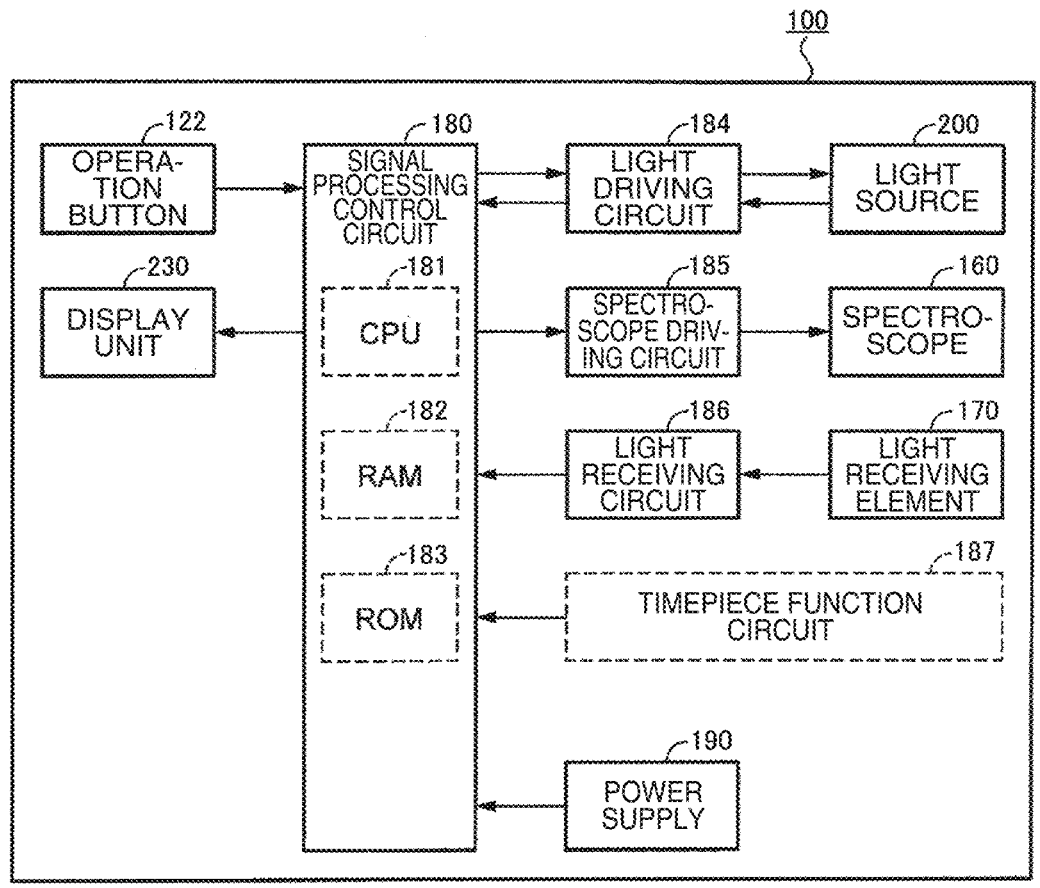
FIG. 21 is a block diagram illustrating the material detecting apparatus.

Next, the configuration and the operation of the material detecting apparatus 100 including a control system will be described with reference to FIG. 21. FIG. 21 is a block diagram illustrating the main configuration of the material detecting apparatus 100 according to the embodiment. The material detecting apparatus 100 includes the signal processing control circuit 180 for controlling the entire control system. The signal processing control circuit 180 includes the central processing unit (CPU) 181, a random access memory 182 (RAM), and a read only memory (ROM) 183.

The above-described sensor chamber 114 includes a sensor chip; and a sensor detector (not illustrated) for detecting whether there is a sensor chip or not and reading a code, and information thereof is sent to the CPU 181 through a sensor detection circuit. When the information is input to the CPU 181, the detection can start. Therefore, the CPU 181 gives an input to the display unit 230 to display an indication indicating that the material detecting apparatus 100 is operable.

When the CPU 181 receives a detection start signal from an operator 122, a light source driving circuit 184 outputs a light source operating signal to operate the light source 200. The light source 200 is equipped with a temperature sensor and a light intensity sensor such that whether the light source 200 is stable or not can be checked. When the light source 200 is stable, the biological gas can be collected into the sensor chamber 114. In order to collect the biological gas, a suction pump (not illustrated) may also be used.

The light source 200 is a laser light source which emits stable linearly polarized light having a single wavelength, and is driven by the light source driving circuit 184 through a signal output from the CPU 181, thereby emitting light. This light is irradiated on the sensor chip 132 through the lens 142, the half mirror 143, and the lens 141. Rayleigh light and Raman scattering light (surface enhanced Raman scattering light; SERS) which is enhanced by an enhanced electric field are incident on the light receiving element 170 through the lens 141, the half mirror 143, the lens 144, the lens 145, the optical filter 150, and the spectroscope 160. The spectroscope 160 is controlled by a spectroscope driving circuit 185. In addition, the light receiving element 170 is controlled by a light receiving circuit 186.

In the optical filter 150, Rayleigh light is blocked, and only SERS light enters into the spectroscope 160. When a wavelength-variable etalon using Fabry-Perot resonance is adopted as the spectroscope 160, a bandwidth ($\lambda 1$ to $\lambda 2$) and a half maximum full-width of permeating light are set. While sequentially and repeatedly changing the wavelength of permeating light from $\lambda 1$ to $\lambda 2$ by the half maximum full-width, the light signal intensity of each half maximum full-width in the light receiving element 170 is converted into an electric signal. As a result, the spectrum of the detected SERS light is obtained.

The obtained spectrum of the SERS light of the detection target material (in the embodiment, acetone) is compared to the fingerprint spectrum stored in the ROM 183 of the signal processing control circuit 180 to specify the target material and to detect the acetone concentration. The signal processing control circuit 180 which functions as a calculating unit calculates the fat combustion amount (health medical information) based on the acetone concentration, and the calculated fat combustion amount is stored in the RAM 182. In order to notify this calculation result to the test subject, the CPU 181 controls the display unit 230 to display the result information. FIG. 20C illustrates an example of the result information.

Regarding a timepiece function for measuring the measurement time, using a well-known timepiece function circuit 187, the current time is obtained and displayed based on a preset time, and the start time and the end time of the fat combustion amount measurement are obtained and displayed based on a fat combustion start signal. In addition, the time piece function is also provided for displaying the fat combustion amount per minute, the integrated amount from the start of the fat combustion measurement, and the like.

It should be easily understood by a person skilled in the art that various modifications can be made in a range not substantially departing from the novel matters and the effects of the invention. Accordingly, such modifications are included in the scope of the invention. For example, a term, which is also described as a different term in a broad sense or a different term having the same meaning at least once in the specification or the drawings, can be replaced with the different term in any position of the specification or the drawings. In addition, the configurations and the operations of the optical device 10, the detecting apparatus or electronic apparatus 100, and the like are not limited to the descriptions of the embodiment, and various modifications can be made. In addition, the invention is applicable to a surface enhanced infrared absorption spectroscopic sensor or the like in addition to the surface enhanced Raman spectroscopy.

The entire disclosure of Japanese Patent Application No. 2013-068252 filed Mar. 28, 2013 is expressly incorporated by reference herein.

What is claimed is:

1. An optical device comprising:
a substrate;
a metal nanostructure on the substrate and contains a plurality of metal particles; and
an organic molecular film on the metal nanostructure,
wherein a particle size of each of the plurality of metal particles is 1 nm to 500 nm when seen in a plan view,
the organic molecular film includes a plurality of holes penetrating through the organic molecular film in a thickness direction,
the plurality of holes are arranged in a two dimensional array on surfaces of the metal particles,
a size $\alpha$ of each of the plurality of holes satisfies $0.5$ nm$\leq\alpha\leq 5$ nm,
a period P of the plurality of holes in the array satisfies $P\leq 10$ nm, and
a thickness t of the organic molecular film satisfies $t\leq 1$ nm.

2. The optical device according to claim 1,
wherein a distance between two adjacent metal particles among the plurality of metal particles is 0.1 nm to 20 nm.

3. The optical device according to claim 1,
wherein the thickness t of the organic molecular film satisfies $t\leq 0.5$ nm.

4. The optical device according to claim 1,
wherein the organic molecular film has a honeycomb structure.

5. The optical device according to claim 4,
wherein the organic molecular film includes a plurality of building block molecules,
each of the building block molecules has, as a basic molecule for forming a high-order compound, a three-fold rotation axis in a molecular center when seen in a plan view, and
three terminals of each of building block molecule which are present at positions rotationally symmetrical to the molecular center are functional groups.

6. The optical device according to claim 5,
wherein the plurality of building block molecules include:
one of trimesic acid molecules, melem molecules, or melamine molecules; or
both the melem molecules and the melamine molecules.

7. A detecting apparatus comprising:
a light source;
the optical device according to claim 1 on which light emitted from the light source is incident; and
a light detector that detects light emitted from the optical device.

8. An electronic apparatus comprising:
the detecting apparatus according to claim 7;
a calculating unit that calculates diagnostic information based on detection information obtained from the detecting apparatus;
a storing unit that stores the diagnostic information; and
a display unit that displays the diagnostic information.

9. An optical device comprising:
a substrate;
a metal nanostructure on the substrate, the metal nanostructure containing a plurality of metal particles; and
a perforated organic molecular film on the metal nanostructure, the perforated organic molecular film providing a two-dimensional array of holes on an outermost surface of each of the metal particles,
wherein a particle size of each of the plurality of metal particles is 1 nm to 500 nm,
a size $\alpha$ of each of the plurality of holes satisfies $0.5$ nm$\leq\alpha\leq 5$ nm,
a period P of the plurality of holes in the array satisfies $P\leq 10$ nm, and
a thickness t of the perforated organic molecular film satisfies $t\leq 1$ nm.

10. The optical device according to claim 9,
wherein a distance between two adjacent metal particles among the plurality of metal particles is 0.1 nm to 20 nm.

11. The optical device according to claim 9,
wherein the thickness t of the perforated organic molecular film satisfies $t\leq 0.5$ nm.

12. The optical device according to claim 9,
wherein the perforated organic molecular film has a honeycomb structure.

13. The optical device according to claim 12,
wherein the perforated organic molecular film includes a plurality of building block molecules,
each of the building block molecules has, as a basic molecule for forming a high-order compound, a three-fold rotation axis in a molecular center, and
three terminals of each of building block molecule which are present at positions rotationally symmetrical to the molecular center are functional groups.

14. The optical device according to claim 13,
wherein the plurality of building block molecules include:
one of trimesic acid molecules, melem molecules, or melamine molecules; or
both the melem molecules and the melamine molecules.

15. A detecting apparatus comprising:
a light source;
the optical device according to claim 9 on which light emitted from the light source is incident; and
a light detector that detects light emitted from the optical device.

16. An electronic apparatus comprising:
the detecting apparatus according to claim 15;
a calculating unit that calculates diagnostic information based on detection information obtained from the detecting apparatus;
a storing unit that stores the diagnostic information; and
a display unit that displays the diagnostic information.

\* \* \* \* \*